US007091260B2

(12) United States Patent
Kühn

(10) Patent No.: US 7,091,260 B2
(45) Date of Patent: Aug. 15, 2006

(54) BONE CEMENT MIXTURE AND X-RAY CONTRAST MEDIUM AS WELL AS METHOD FOR THEIR PREPARATION

(75) Inventor: Klaus-Dieter Kühn, Marburg (DE)

(73) Assignee: Heraeus Kulzer GmbH & Co. KG, Hanau (DE)

(*) Notice: Subject to any disclaimer, the term of this patent is extended or adjusted under 35 U.S.C. 154(b) by 411 days.

(21) Appl. No.: 10/425,337

(22) Filed: Apr. 29, 2003

(65) Prior Publication Data

US 2004/0029996 A1 Feb. 12, 2004

(30) Foreign Application Priority Data

May 29, 2002 (DE) ................................ 102 24 346

(51) Int. Cl.
*A61K 6/083* (2006.01)
*A61K 6/08* (2006.01)
*C08K 9/00* (2006.01)

(52) U.S. Cl. ....................... 523/117; 523/115; 523/205; 526/107; 977/DIG. 1

(58) Field of Classification Search ................ 523/117, 523/115; 526/107
See application file for complete search history.

(56) References Cited

U.S. PATENT DOCUMENTS

| | | | | |
|---|---|---|---|---|
| 6,080,801 | A | 6/2000 | Draenert et al. | 523/115 |
| 6,689,823 | B1 * | 2/2004 | Bellare et al. | 523/115 |
| 6,800,245 | B1 * | 10/2004 | Erbe et al. | 422/1 |
| 2004/0095844 | A1 * | 5/2004 | Miller et al. | 366/130 |

FOREIGN PATENT DOCUMENTS

| | | |
|---|---|---|
| EP | 0 041 614 A1 | 5/1981 |
| EP | 0 089 782 A1 | 3/1983 |
| EP | 0 644 780 B1 | 6/1993 |
| EP | 0 684 222 A1 | 5/1995 |
| WO | WO 93 25245 | 12/1993 |

OTHER PUBLICATIONS

Misra, D.N., "Adsorption of zirconyl salts and their acids on hydroxyapatite: use of the salts as coupling agents to dental polymer composites", Journal of Dental Research, United States, Dec. 1985, vol. 64, No. 12, pp. 1405-1408.
Kim, H.Y. et al, "Improvement of fatigue properties of poly(methyl methacrylate) bone cement by means of plasma surface treatment of fillers", Journal of Biomedical Materials Research, 1999, John Wiley & Sons, Inc., NY, NY, vol. 48, No. 2, 1999, pp. 135-142.
Skrtic, Drago et al, "Physicochemical evaluation of bioactive polymeric composites based on hybrid amorphous calcium phosphates", Journal of Biomedical Materials Research, vol. 53, No. 4, 2000, pp. 381-391.
Kjellson, F. et al, "Tensile properties of a bone cement containing non-ionic contrast media", Journal of Materials Science: Materials in Medicine 2001 Netherlands, vol. 12, No. 10-13, 2001, pp. 889-894.
Abstract of JP 06024927 A.

* cited by examiner

*Primary Examiner*—Tae H. Yoon
(74) *Attorney, Agent, or Firm*—Norris McLaughlin & Marcus PA

(57) ABSTRACT

A bone cement mixture comprised of a polymer component containing an x-ray contrast medium and a monomer component, wherein the x-ray contrast medium is a polymer or copolymer having compounds of radio-opaque elements bonded thereto, or is in the form of substantially spherical polymer or copolymer particles with radio-opaque inorganic nano-particles dispersed therein.

16 Claims, No Drawings

BONE CEMENT MIXTURE AND X-RAY CONTRAST MEDIUM AS WELL AS METHOD FOR THEIR PREPARATION

The invention relates to a bone cement mixture, composed of a polymer component containing an x-ray contrast medium and a monomer component, as well as to an x-ray contrast medium. The invention further relates to a method for preparing the bone cement mixture and the x-ray contrast medium as well as the use of the x-ray contrast medium.

A bone cement mixture in the sense of the invention should be interpreted as a two-component system in which one component exists as a powdery polymer component and the second component as a liquid monomer component. Both components are generally not mixed with each other until right before application.

BACKGROUND OF THE INVENTION

Bone cements, particularly such used to anchor artificial joints, contain x-ray contrast mediums for clinical progress control purposes. Such x-ray contrast mediums allow the surgeon to safely monitor the implant and offer an early diagnosis for possible complications, such as e.g. loosening. Bone cements are chemical resins on acrylate basis (for example Palacos® R from Heraeus Kulzer GmbH & Co. KG). They are offered as two-component systems with a powdery polymer mixture and a liquid monomer. As the contrast agents, zirconium dioxide or barium sulfate are added to the polymer mixture. These x-ray contrast mediums however are not incorporated in the polymer chain and therefore are considered the possible cause for micro-cracks in the cement casing. Zirconium dioxide may possibly have an abrasive effect on contact surfaces.

EP 41 614 describes coated $BaSO_4$ powder for dental fillings, which is prepared by dispersing and adding a polymer solution. EP 89782 describes coated barium sulfate, which is produced by mixing PPMA particles and $BaSO_4$ particles with HEMA and subsequent heating. JP 06024927 relates to polymer filler composites, which are prepared by the polymerization of an acid monomer and another unsaturated monomer in the presence of x-ray contrast medium powder.

WO 0057932: This document describes composites made of a polymeric matrix and solid, liquid or gaseous fillers, which exhibit a “matrix ligament thickness” of preferably less than 250 nm. This signifies the distance between the filler particles. The nano-composites can be produced by introducing the filler into the precursors of the cement, introducing them during the mixing process of the precursors, or introducing them into a prefabricated paste, dough or liquid, where polymerization is induced. The fillers can be radio-opaque, e.g. zirconium oxide.

The examples prove composites with the following particles: 1–3 micrometer $BaSO_4$, 100 nm $BaSO_4$, and 60 nm $Al_2O_3$ (acrylic-coated).

EP 644 780: Claim 12 relates to a granulate or fibrous material, where the filler particles (size of 1–15μ) are enclosed at least partially by the (co)polymeric matrix, wherein the polymer chains are not cracked. The material can be produced through mixing and extrusion.

U.S. Pat. No. 6,080,801 reveals polymer granules (FIG. 1) with micro-fillers embedded partially or completely therein. These granules are no larger than 300μ and contain filler particles of the size 1–250, preferably 5–15μ. They are produced e.g. when the filler particles form crystallization nuclei during polymerization.

SUMMARY OF THE INVENTION

The invention is based on the task of making an improved x-ray contrast agent and a bone cement containing said agent as well as method for their preparation available.

Pursuant to the invention this task is resolved with the features of the independent claims. The x-ray contrast agent is designed a) as a polymer or copolymer with compounds of radio-opaque elements chemically bonded thereto, or b) as largely spherical polymer or copolymer particles with radio-opaque inorganic nanoparticles dispersed therein of a particle size of 3–15 nm, prepared through polymerization, preferably suspension polymerization, in the presence of nano-particles, wherein the nano-particles are covered completely or almost completely by the (co)polymer material.

DETAILED DESCRIPTION

Bone cement mixtures containing such x-ray contrast agents, wherein said mixtures are composed of a polymer component and a monomer component, with the polymer component comprising polymers and/or copolymers, are prepared pursuant to the invention in that during preparation of the polymers and/or copolymers a polymer and/or monomer containing radio-opaque elements or radio-opaque inorganic nano-particles with a particle size of 3–15 nm are added.

When the x-ray contrast agent is produced by polymerizing zirconyl-di-methacrylate and/or other methacrylates containing zirconium and/or other radio-opaque elements into a polymer or copolymer, x-ray contrast agents or bone cement mixtures prepared this way contain no mineral components that cause the above-mentioned disadvantages since the resulting x-ray contrast agent pursuant to the invention is produced as a polymer or copolymer.

Even when the x-ray contrast means contains radio-opaque inorganic nano-particles of a particle size of 3–15 nm with an outer polymer layer are problems caused by abrasion avoided.

It has proven useful that the x-ray contrast medium contains zirconium and/or barium and/or other radio-opaque elements, in particular zirconyl-di-methacrylate and/or other methacrylates containing zirconium and/or other radio-opaque elements.

In particular zirconyl-di-methacrylate is polymerized into the polymer or copolymer and added to the polymer component. Polymer or copolymers containing barium and/or zirconium and/or radio-opaque elements can be used pursuant to the invention as radiographic contrast media in bone cement mixtures.

When the x-ray contrast agent is introduced into the (co)polymer as inorganic nano-particles, it has proven useful if the inorganic nano-particles are surface-modified, preferably with suitable silanes known to the expert. The nano-particles can have spherical, ellipsoid, plate-like or irregular shapes. The inorganic nano-particles preferably consist essentially of $ZrO_2$.

The following describes examples of embodiments of the invention.

A monomer component common in bone cements is used as the monomer component. The polymer component is produced from a copolymer with 20% zirconyl-di-methylacrylate and an initiator, which represents approximately 1% of the polymer component.

In a second example, the polymer component is made from a copolymer with 40% zirconyl-di-methacrylate, a polymer made of polymethyl-methacrylate or copolymers and an initiator, wherein the copolymer containing zirconyl-di-methacrylate represents 50%, the polymer 49% and the initiator 1% of the overall component.

A third example contains the same components as the second example, wherein the copolymer contains an 80% portion of zirconyl-di-methacrylate and represents 25% in the overall mixture of the polymer component, while the polymer represents 74% and the initiator 1%.

Instead of the zirconyl-di-methacrylate other zirconium-containing acrylates can be used as well. The opacity of the material can be adjusted with the zirconium (or barium) content.

A bone cement mixture pursuant to the invention with inorganic nano-particles of a particles size of 3–15 nm can be obtained for example by using a monomer component conventionally used for bone cements as the monomer component, and by introducing therein a polymer component with (co)polymer particles with radio-opaque inorganic nano-particles dispersed therein.

The (co)polymer particles with radio-opaque inorganic nano-particles dispersed therein are prepared in advance by subjecting monomers to suspension polymerization in the presence of coated or uncoated $ZrO_2$ particles of the particle size 7 nm. This creates spherical polymer or copolymer particles with radio-opaque inorganic nano-particles dispersed therein. The percentage of $ZrO_2$ particles present in the (co)polymer that is obtained this way is e.g. 15%. The polymer component for the bone cement is now prepared from the above-described spherical polymer or copolymer particles with the radio-opaque inorganic nano-particles dispersed therein and an initiator, which represents about 1% of the polymer component.

In another example for a bone cement mixture with inorganic nano-particles of the particle size 3–15 nm, a monomer component common for bone cements is used. The polymer component consists of (co)polymer particles with radio-opaque inorganic nano-particles dispersed therein and of spherical polymer or copolymer particles without radiographic contrast medium and of an initiator.

The (co)polymer particles with radio-opaque inorganic nano-particles dispersed therein are prepared in advance by subjecting conventional monomers to suspension polymerization in the presence of coated or uncoated $ZrO_2$ particles of the particle size 7 nm. This creates spherical polymer or copolymer particles with radio-opaque inorganic nano-particles dispersed therein. The portion of $ZrO_2$ particles dispersed in the (co)polymer obtained this way is e.g. 30%. The polymer component for the bone cement is now prepared from the above-described spherical polymer or copolymer particles with radio-opaque inorganic nano-particles dispersed therein at a ratio of 50% and spherical polymer or copolymer particles without radiographic contrast medium at a ratio of 49% and an initiator, which represents roughly 1% of the polymer component.

By adding non-radio opaque (co)copolymer, the radio-opacity of the bone cement mixture can be adjusted such that the radio-opacity level corresponds to an amount of about 5–45%, preferably 8–16% x-ray contrast medium in the polymer component of the bone cement.

I claim:

1. Bone cement mixture composed of a polymer component containing an x-ray contrast medium, and a monomer component, wherein the x-ray contrast medium a) is a polymer or copolymer having compounds of radio-opaque elements bonded thereto, or b) is in the form of substantially spherical polymer or copolymer particles having radio-opaque inorganic nano-particles of the particle size 3–15 nm dispersed therein, wherein the nano-particles are covered completely or substantially completely by the (co)polymer material.

2. Bone cement mixture according to claim 1, wherein said substantially spherical polymer or copolymer particles are produced by polymerization in the presence of said nano-particles.

3. Bone cement mixture according to claim 2, wherein said polymerization is a suspension polymerization.

4. Bone cement mixture according to claim 1, wherein the inorganic nano-particles are surface-modified.

5. Bone cement mixture according to claim 4, wherein said inorganic nano-particles are surface modified with silanes.

6. Bone cement mixture according to claim 1, wherein the inorganic nano-particles consist essentially of $ZrO_2$.

7. Bone cement mixture according to claim 1, wherein the nano-particles have a spherical, ellipsoid, plate-shaped or irregular shape.

8. Bone cement mixture according to claim 1, wherein the x-ray contrast medium contains zirconium and/or barium end/or other radio-opaque elements.

9. Bone cement mixture according to claim 1, wherein the x-ray contrast medium contains zirconyl-di-methacrylate and/or other methacrylates containing zirconium and/or other radio-opaque elements.

10. X-ray contrast medium comprising substantially spherical polymer or copolymer particles with radio-opaque inorganic nanoparticles of a particle size of 3–15 nm dispersed therein, wherein the nano-particles are covered completely or almost completely by the polymer or copolymer material.

11. The X-ray contrast medium of claim 10, wherein said substantially spherical polymer or copolymer particles with radio-opaque inorganic nanoparticles dispersed therein are prepared by polymerization in the presence of said nano-particles.

12. The X-ray contrast medium of claim 11, wherein said polymerization is a suspension polymerization.

13. X-ray contrast medium according to claim 10, comprising barium and/or zirconium and/or other radio-opaque elements.

14. X-ray contrast medium pursuant to claim 10, comprising zirconyl-di-methacrylate and/or other methacrylates containing zirconium and/or other radio-opaque elements.

15. Method for producing bone cement mixtures of a polymer component and a monomer component, wherein the polymer component contains polymers and/or copolymers, which comprises preparing of the polymers and/or copolymers in the presence of a polymer and/or monomer containing radio-opaque element.

16. Method pursuant to claim 15, wherein during the production zirconyl-di-methacrylate and/or other methacrylates containing zirconium and/or other radio-opaque elements are polymerized into a polymer or copolymer and added to the polymer component.

* * * * *

UNITED STATES PATENT AND TRADEMARK OFFICE

CERTIFICATE OF CORRECTION

PATENT NO. : 7,091,260 B2
APPLICATION NO. : 10/425337
DATED : August 15, 2006
INVENTOR(S) : Kuhn It is certified that error appears in the above-identified patent and that said Letters Patent is hereby corrected as shown below:

In the Claims

Column 4, Line 29, “end/or” should read -- and/or --

Signed and Sealed this
Twenty-fifth Day of February, 2014

Michelle K. Lee
*Deputy Director of the United States Patent and Trademark Office*